United States Patent
Sebag et al.

(10) Patent No.: US 6,403,106 B1
(45) Date of Patent: Jun. 11, 2002

(54) COSMETIC USE OF COPOLYMERS WITH A RIGID HYDROPHILIC BACKBONE GRAFTED BY FLEXIBLE HYDROPHOBIC MACROMONOMERS, AND COMPOSITIONS THEREFOR

(75) Inventors: Henri Sebag; Nathalie Mougin, both of Paris; Bertrand Lion, Livry-Gargan; Jean Mondet, Aulnay-sous-Bois, all of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/155,297

(22) PCT Filed: Feb. 25, 1997

(86) PCT No.: PCT/FR97/00335

§ 371 (c)(1),
(2), (4) Date: Nov. 18, 1998

(87) PCT Pub. No.: WO97/35541

PCT Pub. Date: Oct. 2, 1997

(30) Foreign Application Priority Data

Mar. 27, 1996 (FR) .............................. 96 03814

(51) Int. Cl.$^7$ ............................ A61K 6/00; A61K 7/00; A61K 9/04; A61K 9/00; A61K 7/42
(52) U.S. Cl. ......................... 424/401; 424/45; 424/47; 424/59; 424/70.1; 424/70.9; 424/63; 424/70.16; 424/70.11; 424/70.17
(58) Field of Search ............................ 424/401, 45, 47, 424/59, 70.1, 70.9, 63, 70.16, 70.11, 70.17

(56) References Cited

U.S. PATENT DOCUMENTS

| 4,015,612 A | | 4/1977 | Pavlik et al. |
| 4,496,708 A | | 1/1985 | Dehm et al. |
| 5,053,461 A | * | 10/1991 | Tone et al. .................. 525/80 |
| 5,061,481 A | * | 10/1991 | Suzuki et al. ................. 424/63 |
| 5,116,910 A | * | 5/1992 | Tone et al. .................. 525/80 |
| 5,280,073 A | * | 1/1994 | Siol et al. ..................... 525/80 |

FOREIGN PATENT DOCUMENTS

| WO | WO92/16187 | * | 10/1992 |
| WO | WO 92/16187 | | 10/1992 |
| WO | WO 96/00562 | | 1/1996 |

OTHER PUBLICATIONS

"Free Radical Telomerization" C. M. Starks 1974 pp. 4–7, 199–200.*

* cited by examiner

Primary Examiner—Thurman K Page
Assistant Examiner—Humera N. Sheikh
(74) Attorney, Agent, or Firm—Finnegan, Henderson, Farabow, Garrett & Dunner, L.L.P.

(57) ABSTRACT

The subject-matter of the present invention is the use, in and for the preparation of cosmetic or dermatological compositions, of a grafted copolymer, the skeleton (S) of which is composed of a hydrophilic copolymer, with a glass transition temperature Tg greater than 25° C., obtained by radical polymerization or by polycondensation, comprising, on the chain of the skeleton (S), at least one graft composed of a hydrophobic macromonomer (M) with a glass transition temperature T'g of less than 25° C., as well as the cosmetic or dermatological compositions employed.

34 Claims, No Drawings

COSMETIC USE OF COPOLYMERS WITH A RIGID HYDROPHILIC BACKBONE GRAFTED BY FLEXIBLE HYDROPHOBIC MACROMONOMERS, AND COMPOSITIONS THEREFOR

This application is a 371 of PCT/FR 97/00335 filed Feb. 25, 1997.

The present invention relates to the use of copolymers with a stiff hydrophilic skeleton which are obtained by radical polymerization or by polycondensation and which are grafted by flexible hydrophobic macromonomers in and for the preparation of cosmetic or dermatological compositions, and to the compositions employed.

For numerous cosmetic applications, in particular those intended for the treatment and care of the hair, skin or eyelashes, use is made of polymers capable, after application to the substrate to be treated and drying, of forming a deposit having mechanical properties and adhesive properties. From this viewpoint, the aim is to find polymers with a hydrophilic nature, in order to be easily removed under the action of an aqueous solution of surfactants. At the same time, the aim is to obtain a hydrophobic surface deposit in order, on one hand, to withstand the surrounding moisture, in particular a deposit which is non-hygroscopic to the touch, a deposit which withstands rain (hair applications or skin applications) or a deposit which withstands lachrymal fluid (mascaras). On the other hand, the aim is to find a hydrophobic deposit in order to introduce cosmetic properties, such as softness to the touch, generally conferred by hydrophobic substances in cosmetics.

In order to combine all these characteristics, polymers of different hydrophilicity and of different hydrophobicity are generally mixed or else a hydrophilic polymer is used in combination with a hydrophobic substance. It is generally difficult to completely control the stratification of these mixtures after drying the deposit in order to obtain both good mechanical and adhesive properties and a hydrophobic surface.

Another problem relating to the deposited polymers arises in the hair field, in particular in the context of products for form retention of or for setting the hair. This is because it is often difficult to adjust the properties of the polymer which has to be deposited in order to simultaneously obtain good setting of the hair, good hold of this setting and easy removal on combing or brushing. This is because, in order to achieve good setting of the hair, the setting polymer is plasticized in order to bring its phase transition temperature to room temperature. Under these conditions, removal on brushing or combing is then difficult.

One of the objectives of the present invention is thus to use, in cosmetic or dermatological compositions, polymers having satisfactory film-forming properties which give a hydrophobic surface and which can be easily removed under the action of an aqueous solution of surfactants.

Another objective of the invention is to use, in and for the preparation of hair styling compositions, polymers having both significant characteristics of setting which are highly resistant to slight mechanical stresses and good stiffness, without it being necessary to add a plasticizer or at least with small amounts of plasticizer, in order subsequently to be removed very easily on brushing or combing.

The inventors have discovered, surprisingly, that these objectives could be achieved by using, in and for the preparation of cosmetic or dermatological compositions, specific grafted copolymers, the skeleton of which is hydrophilic and stiff and composed of a copolymer obtained by radical polymerization or by polycondensation, comprising, on the chain of the skeleton, at least one flexible hydrophobic macromonomer graft.

The subject-matter of the present invention is the use, in and for the preparation of cosmetic or dermatological compositions, of a grafted copolymer, the skeleton (S) of which is composed of a hydrophilic copolymer, with a glass transition temperature Tg greater than 25° C., obtained by radical polymerization or by polycondensation, comprising, on the chain of the skeleton (S), at least one graft composed of a hydrophobic macromonomer (M) with a glass transition temperature T'g of less than 25° C.

The present invention also relates to cosmetic or dermatological compositions containing, in a cosmetically acceptable medium, at least one grafted copolymer, the skeleton (S) of which is composed of a hydrophilic copolymer, with a glass transition temperature Tg greater than 25° C., obtained by radical polymerization or by polycondensation, comprising, on the chain of the skeleton, at least one graft composed of a hydrophobic macromonomer (M) with a glass transition temperature T'g of less than 25° C.

Other subject-matters will become apparent in the light of the description and examples which follow.

"Hydrophilic copolymer" is understood to mean, throughout the text of the description, any copolymer which is soluble or dispersable in water, lower ($C_1$–$C_4$) alcohols or mixtures of water and of lower alcohol(s).

"Hydrophobic polymer" is understood to mean, throughout the text of the description, any polymer which is insoluble in water, lower ($C_1$–$C_4$) alcohols or mixtures of water and of lower alcohol(s).

"Macromonomer" is understood to mean, throughout the text of the description, any oligomer comprising, on just one end, either a group possessing ethylenic unsaturation capable of polymerizing by the radical route with the monomers constituting the skeleton (S) of the copolymer of the invention and of grafting onto the polymeric chain of the skeleton (S); or a reactive functional group capable of reacting with the monomers (A) and (B) of the skeleton (S) or else with the preformed skeleton (S).

The macromonomers (M) grafted by covalent bonding to the polymeric chain of the skeleton (S) of the copolymers of the invention are preferably chosen from hydrocarbon-comprising, hydrofluorocarbon comprising or fluorocarbon-comprising macromonomers having a glass transition temperature T'g of less than 25° C.

The macromonomers (M) have a glass transition temperature T'g preferably of less than or equal to 10° C. and more particularly of less than or equal to 0° C.

Furthermore, the macromonomers (M) are hydrophobic, that is to say insoluble in water, and have a surface tension generally of less than or equal to 40 dyne/cm at 20° C.

They preferably exhibit an average molecular weight, measured at the peak tip by steric exclusion chromatography, ranging from 200 to 20,000.

Mention may be made, among the macromonomers (M) grafted onto the copolymers of the invention, of:

(a) polymers and copolymers of linear or branched $C_2$–$C_{18}$ alkyl acrylate or methacrylate with a T'g of less than 25° C. and exhibiting a terminal group chosen from vinyl, allyl, methallyl, (meth)acryloyl, ethacryloyl, vinylbenzoyl, vinylbenzyl, $C_1$–$C_4$ alkenyl or $C_1$–$C_6$ cycloalkenyl or a terminal reactive functional group capable of interacting with the skeleton (S) or the monomers constituting it (such as —OH, —$NH_2$, —COOH or S anhydride) or a terminal reactive functional group capable of participating in a polycondensation (such as diol, diamine or dicarboxylic acid), among which may in particular be mentioned: poly (butyl acrylate) macromonomers with a monomethacrylate end, such as the products sold under the name [lacuna] by the company Toa Gosei; poly (butyl acrylate) macromonomers with a monomethacrylate end; poly(2-ethylhexyl acrylate) macromonomers with a monoacrylate or monomethacrylate end; poly(dodecyl acrylate) or poly (dodecyl methacrylate) macromonomers; or poly (stearyl acrylate) or poly(stearyl methacrylate) macromonomers;

(b) polyolefins with a T'g of less than 25° C. and exhibiting a terminal group possessing ethylenic unsaturation or a terminal reactive functional group capable of interacting with the skeleton (S) or the monomers constituting it or a terminal reactive functional group capable of participating in a polycondensation, among which mention may in particular be made of:

polyethylene macromonomers; polypropylene macromonomers; polyethylene/polypropylene copolymer macromonomers; polyethylene/polybutylene copolymer macromonomers; polyisobutylene macromonomers; polybutadiene macromonomers; polyisoprene macromonomers; or polyolefin macromonomers possessing a very short chain, such as, for example, hydrogenated polybutadiene or hydrogenated polyisoprene macromonomers comprising only 3 or 4 repeat units and more particularly phytol (3,7,11,15-tetramethylhexadec-2-en-1-ol) acrylate or methacrylate.

(c) vinyl polymers with a T'g of less than 25° C. and exhibiting a terminal group possessing ethylenic unsaturation or a terminal reactive functional group capable of interacting with the skeleton (S) or the monomers constituting it or a terminal reactive functional group capable of participating in a polycondensation;

(d) polymers or copolymers of fluorinated or perfluorinated monomers with a T'g of less than 25° C. and exhibiting a terminal group possessing ethylenic unsaturation or a terminal reactive functional group capable of interacting with the skeleton (S) or the monomers constituting it or a terminal reactive functional group capable of participating in a polycondensation, among which mention may particularly be made of perfluoroalkyl (meth)acrylate homopolymers or copolymers;

(e) polyesters with a T'g of less than 25° C. and exhibiting a terminal group possessing ethylenic unsaturation or a terminal reactive functional group capable of interacting with the skeleton (S) or the monomers constituting it or a terminal reactive functional group capable of participating in a polycondensation, among which mention may in particular be made of aliphatic polyesters composed of long carbonaceous sequences, such as polyesters of 12-hydroxystearic acid or polysebacates of aliphatic diols composed of long carbonaceous sequences (for example hexanediol).

The macromonomers (M) are present in the composition of the copolymers of the invention in a proportion preferably ranging from 1 to 60% by weight with respect to the total weight of the grafted copolymer.

The grafted copolymers in accordance with the present invention preferably exhibit an average molecular weight, measured at the peak tip by steric exclusion chromatography, ranging from 10,000 to 5,000,000.

They are generally hydrophilic, namely soluble or dispersable in aqueous media or alcoholic or aqueous/alcoholic media based on lower alcohols. They can be non-ionic, anionic, cationic or amphoteric, the ionic groups preferably being situated in the structure of the skeleton (S) in order to introduce hydrophilicity.

The skeleton (S) of the copolymers of the invention has a phase transition temperature Tg of greater than 25° C. and preferably of greater than or equal to 35° C.

The skeleton (S) of the copolymers of the invention is composed of a copolymer obtained by radical polymerization or by polycondensation.

The skeleton (S) obtained by the radical route preferably results from the polymerization:

(a) of at least one monomer or one mixture of monomers (A) possessing ethylenic unsaturation, and (b) of at least one monomer or one mixture of monomers (B) which are polar and hydrophilic and which possess ethylenic unsaturation, the monomers (A) and (B) being chosen so that the phase transition temperature Tg of the skeleton (S) is greater than 25° C.

The monomers of the type (A) are chosen, for example, from the group consisting of:

acrylic or methacrylic esters or amides obtained from linear, branched or cyclic aliphatic alcohols and/or from aromatic alcohols, preferably $C_{1-4}$ alcohols, such as methyl (meth)acrylate, ethyl (meth)acrylate, propyl (meth)acrylate, butyl (meth)acrylate, isobutyl (meth) acrylate, tert-butyl (meth)acrylate or tert-butylacrylamide;

vinyl, allyl or methallyl esters or amides obtained from linear, branched or cyclic aliphatic alcohols and/or from aromatic alcohols, preferably $C_1$–$C_6$ alcohols, such as vinyl acetate, vinyl propionate, vinyl benzoate or vinyl tert-butylbenzoate;

olefins, such as ethylene, propylene, styrene or substituted styrene;

fluorinated or perfluorinated acrylic or vinyl monomers; their mixtures.

The monomers of the type (B) of the invention are chosen from anionic, cationic, amphoteric or non-ionic, hydrophilic and polar monomers possessing ethylenic unsaturation, or their mixtures.

Mention may be made, among the anionic monomers (B), of:

monomers comprising at least one acidic functional group, in the free form or else in the partially or completely neutralized form, such as monocarboxylic acids, such as acrylic, methacrylic or crotonic acid; dicarboxylic acids or acid anhydrides, as well as their monoesters or monoamides, such as maleic anhydride, in the diacid, monoester or monoamide form, or itaconic acid;

monomers comprising at least one sulphonic acid functional group, in the free form or else in the partially or completely neutralized form, such as vinyl- or styrenesulphonic acid or 2-acrylamido-2-methylpropanesulphonic acid;

monomers comprising at least one phosphoric or phosphonic acid functional group, in the free form or else in the partially or completely neutralized form.

The anionic monomers (B) are preferably partially or completely neutralized by a monobasic compound, such as an inorganic base, for example sodium hydroxide or potassium hydroxide, or an aminoalcohol, for example taken from the group consisting of 2-amino-2-methyl-1-propanol (AMP), triethanolamine, triisopropanolamine (TIPA), monoethanolamine, tri(2-hydroxypropyl)amine, 2-amino-2-methyl-1,3-propanediol (AMPD) or 2-amino-2-hydroxymethyl-1,3-propanediol.

Mention may be made, among the cationic monomers (B), of:

monomers comprising an amine functional group, in the free form or else partially or completely neutralized or else partially or completely quaternized, such as dimethylaminoethyl (meth)acrylate, dimethylaminoethylmethacrylamide, vinylamine, vinylpyridine or diallyldimethylammonium chloride.

The cationic monomers (B) are preferably partially or completely neutralized by an inorganic or organic acid, such as hydrochloric, acetic, lactic or glycolic acid, or else partially or completely quaternized by an alkyl, cycloalkyl or aryl halide or a dialkyl sulphate (dimethyl or diethyl sulphate).

Mention may be made, among the amphoteric monomers (B), of carboxybetaines or sulphobetaines obtained by partial or complete quaternization of monomers possessing ethylenic unsaturation comprising an amine functional group by sodium salts of carboxylic acids possessing a mobile halide (sodium chloroacetate) or by cyclic sultones (propanesultone).

Mention may be made, among the non-ionic monomers (B), of:

$C_1$–$C_4$ hydroxyalkyl (meth)acrylates, such as 2-hydroxyethyl (meth)acrylate or 2-hydroxypropyl (meth) acrylate, acrylamides, such as acrylamide, methacrylamide or di ($C_1$–$C_4$) alkyl (meth) acrylamides;

N-vinylpyrrolidone;

ethylene glycol (meth)acrylate, diethylene glycol (meth) acrylate or (meth)acrylates of polyethylene glycol possessing a hydroxyl or ether end.

The skeleton (S) obtained by polycondensation preferably results from the reaction:

(a) of at least one monomer or one mixture of monomers (A') which is polycondensable and optionally (b) of a monomer or a mixture of monomers (B'), which is polycondensable with the monomer or monomers (A'), carrying at least one hydrophilic functional group contributing solubility or dispersabilty in water, alcoholic media or aqueous/alcoholic media, the monomers (A') and (B') being chosen so that the phase transition temperature Tg of the skeleton (S) is greater than 25° C.

The skeletons (S) of the polycondensate type are chosen, for example, from polyesters, polyamides, polyurethanes or polyesteramides.

The grafted copolymers in accordance with the invention can be obtained by direct radical copolymerization of monomers (A) and (B) as defined above constituting the skeleton (S) and of a macromonomer (M) exhibiting, on just one end, a group possessing ethylenic unsaturation which is copolymerizable with the monomers (A) and (B).

The direct radical polymerization can then be carried out in solution in a mutual solvent or a mixture of mutual solvents. It can also be carried out in heterogeneous medium, in particular in suspension or in emulsion in water, the macromonomer being dissolved in the mixture with the monomers (A) and (B) as defined above.

When the skeleton (S) is a polycondensate, such as a polyester, a polyamide, a polyurethane or a polyesteramide, the grafted copolymers in accordance with the invention can be obtained by direct polycondensation of monomers (A') and (B') as defined above constituting the skeleton (S) and of a macromonomer (M) exhibiting, on just one end, two terminal reactive functional groups (for example, diol, diamine, dicarboxylic acid or acid anhydride) which are capable of polycondensating with the monomers (A') and (B').

The direct polycondensation can be carried out in solution, in dispersion or in molten medium, according to a reaction of the esterification, amidation, transesterification or transamidation type.

Finally, the grafted copolymers in accordance with the invention can also be obtained by reacting the copolymer of the skeleton (S), synthesized beforehand, with a macromonomer (M) exhibiting an appropriate reactive terminal functional group, preferably a monofunctional one (amine, alcohol, carboxylic acid, anhydride, epoxy, and the like), capable of interacting with the skeleton (S). The reaction is generally carried out in solution or in a molten medium.

The cosmetic and dermatological compositions according to the invention thus comprise, in a cosmetically acceptable vehicle, the polymers as described above for applications as varied as those encountered, for example, in the hair or make-up field or alternatively the field of caring for the skin or any other cosmetic field in which the use of a film-forming substance is desirable or sought after.

The grafted copolymers according to the invention can be used alone as film-forming agent or else as additive in conventional film-forming agents in and for the preparation of cosmetic or dermatological compositions.

Mention may more particularly be made, among the applications preferably targeted by the present invention, of:

the field of hair products (washing, caring for or beautifying the hair), where the compositions according to the invention can be provided in the form of aerosols, of foams, of shampoos, of conditioners, of styling or treating lotions or gels, or of hair-shaping or hair-setting or alternatively fixing lacquers or lotions.

the field of make-up products, in particular for making up the nails, eyelashes or lips, where the compositions according to the invention can be provided in the form of nail varnishes, of mascaras or eyeliners, or of lipsticks.

in the field of skin care products (creams, milks, lotions, masks, serums or anti-sun products).

The concentration of grafted copolymer in the cosmetic or dermatological compositions of the invention is generally between 0.1 and 50% and preferably between 1 and 30% by total weight of the composition. It varies according to the cosmetic or dermatological application envisaged.

In the case of nail varnishes, this proportion is generally greater than or equal to 30% by weight when the copolymer of the invention is used alone as film-forming agent.

The cosmetically acceptable vehicle for the compositions according to the invention is preferably composed of water, of one or more cosmetically acceptable organic solvents or else of a mixture of water and of one or more cosmetically acceptable organic solvents.

Use is more particularly made, among these organic solvents, of lower $C_1$–$C_4$ alcohols, such as ethanol.

The grafted copolymers according to the invention are dissolved or in dispersion in the vehicle for the compositions of the invention.

The compositions can in addition and of course comprise various adjuvants intended to render it acceptable in a specific cosmetic application.

The compositions according to the invention can comprise conventional cosmetic additives chosen from fatty substances, such as mineral, vegetable, animal or synthetic oils, animal, fossil, vegetable, mineral or synthetic waxes, organic solvents, thickening agents, softeners, antifoaming agents, moisturizing agents, humectants, treating agents (agents for combating hair loss, antidandruff agents, and the like), antiperspirants, basifying agents, UV-A or UV-B or broad spectrum sunscreens, dyes, pigments, fragrances, plasticizers, preservatives, anionic, non-ionic or amphoteric organic polymers which are compatible with the grafted copolymers of the invention, and propellants, when the compositions are provided in the aerosol form.

Of course, a person skilled in the art will take care to choose the optional additional compound or compounds mentioned above so that the advantageous properties intrinsically attached to the compositions according to the invention are not, or not substantially, detrimentally affected by the envisaged addition or additions.

Another subject-matter of the invention is a process for the cosmetic treatment of keratinous substances, such as the skin, hair, scalp, eyelashes, eyebrows, nails or lips, characterized in that it consists in applying, to the latter, a composition as defined above.

The examples which follow serve to illustrate the invention without, however, exhibiting a limiting nature.

PREPARATION EXAMPLES 1 TO 6

EXAMPLE 1

Preparation of a Poly(2-ethylhexyl acrylate) Telomer with an OH Ending and with a Molecular Weight of 1150

The following are successively introduced into a reactor with nitrogen sparging, a reflux condenser, a central mechanical stirrer and a thermometer: 52.1 g of 2-ethylhexyl acrylate, 100 g of tetrahydrofuran, 3.9 g of mercaptoethanol and 0.5 g of azobisisobutyronitrile. The mixture is homogenized with stirring at room temperature with nitrogen sparging. The mixture is subsequently heated with stirring to 66° C., while maintaining nitrogen sparging, and is left to react under these conditions for 24 hours. At the end of the synthesis, the mixture is brought back to room temperature, the solvent is evaporated at atmospheric pressure in the reactor and then the mercaptoethanol residues are distilled off by establishing a vacuum of $10^{-2}$ millibar. The telomer is thus obtained in the form of an oil.

The final hydroxyl number is 48.9, which corresponds to a molecular weight of 1150 for a functionality of 1.

The characterization of the distribution of the molecular weights by steric exclusion chromatography in tetrahydrofuran gives 4 main peaks at 1720, 700, 460 and 170.

EXAMPLE 2

Preparation of a Macromonomer (M) with an Acrylate Ending Obtained from the Telomer of Example 1

30 g of telomer of Example 1 (0.0262 mol), 3.2 g of triethylamine and 60 g of toluene are introduced into a 500 ml reactor with a central stirrer, a thermometer and a reflux condenser. 2.85 g (0.0312 mol) of acryloyl chloride in 10 g of toluene contained in a dropping funnel are placed above the reactor. The reactor is cooled to 5° C. and the acryloyl chloride solution is introduced dropwise while maintaining the temperature below 10° C. Once the addition has been carried out, the mixture is allowed to return to room temperature with stirring and the reaction is maintained for 18 hours.

The solution obtained is filtered through sintered glass in order to remove the triethylamine hydrochloride precipitate. The filtrate obtained is diluted with 500 ml of methylene chloride and extracted twice with water. After extracting, the solution is freed from the solvent by evaporation under vacuum on a rotary evaporator.

An overall yield of 80% (telomerization stage of Example 1 and functionalization stage) is thus obtained. The product is provided in the form of an oil.

The characterization of the distribution of the molecular weights by steric exclusion chromatography in tetrahydrofuran gives 4 main peaks at 1900, 880, 580 and 350.

The theoretical glass transition temperature T'g of this macromonomer is below −50° C. according to the Polymer Handbook, 3rd edition, Wiley Interscience.

EXAMPLE 3

Preparation of a Poly(2-ethylhexyl acrylate) Telomer with an OH Ending and with a Molecular Weight of 4650

The preparation is carried out under the same conditions as Example 1, using 52.1 g of 2-ethylhexyl acrylate, 100 g of tetrahydrofuran, 1 g of mercaptoethanol and 0.45 g of azobisisobutyronitrile.

The final hydroxyl number is 72, which corresponds to a molecular weight of 4650 for a functionality of 1.

EXAMPLE 4

Preparation of a Macromonomer (M) with an Acrylate Ending Obtained from the Telomer of Example 3

The preparation is carried out under the same conditions at Example 2, using:

in the reactor: 30 g of telomer of Example 3 (0.0066 mol), 0.78 g of triethylamine and 70 g of toluene;

in the dropping funnel: 0.7 g (0.0079 mol) of acryloyl chloride in 10 g of toluene.

An overall yield of 80% (telomerization stage of Example 3 and functionalization stage) is thus obtained. The product is provided in the form of an oil.

The characterization of the distribution of the molecular weights by steric exclusion chromatography gives 1 single main peak corresponding to a molecular weight of 4300.

The theoretical glass transition temperature T'g of this macromonomer is below −50° C. according to the Polymer Handbook, 3rd edition, Wiley Interscience.

EXAMPLE 5

Preparation of a Grafted Acrylic Copolymer from the Macromonomer (M) of Example 2

The grafted acrylic copolymer is prepared from the following composition:

| | |
|---|---|
| tert-Butyl acrylate | 60% by weight |
| Acrylic acid | 20% by weight |
| Macromonomer (M) of Example 2 | 20% by weight |

100 g of the mixture of monomers described above, 100 g of ethanol and 1 ml of 97% tert-butyl peroxy(2-ethylhexanoate) (sold by the company Akzo under the name Trigonox 21 S) are introduced into a reactor with a central stirrer, a reflux condenser, a thermometer and nitrogen sparging. The mixture is stirred at room temperature under nitrogen sparging in order to be homogenized. It is then brought to reflux (78° C.) with stirring and nitrogen sparging. Reaction is allowed to take place under these conditions for 18 hours. At the end of the synthesis, the mixture is returned to room temperature and diluted with approximately 50 ml of ethyl acetate, and the polymer is purified by precipitation of the solution from 8 l of petroleum ether. The precipitate is dried under vacuum at a temperature of 50° C. to constant weight.

The yield is 80%. The acid number is 168.5.

The characterization of the distribution of the molecular weights by steric exclusion chromatography gives 1 single main peak corresponding to a molecular weight of 101,000.

The glass transition temperature Tg of the skeleton, measured by DSC (differential scanning calorimetry) is 73° C.

EXAMPLE 6
Preparation of a Grafted Acrylic Copolymer from the Macromonomer (M) of Example 4

The grafted acrylic copolymer is prepared from the following composition:

| tert-Butyl acrylate | 60% by weight |
|---|---|
| Acrylic acid | 20% by weight |
| Macromonomer (M) of Example 4 | 20% by weight |

The preparation is carried out under the same conditions as Example 5.

The yield is 85%. The acid number is 180.

The characterization of the distribution of the molecular weights by steric exclusion chromatography gives 1 single main peak corresponding to a molecular weight of 115,400.

The glass transition temperature Tg of the skeleton, measured by DSC (differential scanning calorimetry) is 90° C.

EXAMPLE 7
Preparation of a Polyisobutylene Macromonomer (P) Possessing an Acrylamido Ending The starting material is a commercial product sold under the name Kerocom PIBA by the company [lacuna] which is a polyisobutylene macromonomer with a primary amine end, the mass of which, measured by steric exclusion chromatography on microstyragel columns with tetrahydrofuran as eluent and polystyrene standards, is equal to 2000 at the GPC peak tip. In order to obtain a macromonomer which can be polymerized by the radical route, this polyisobutylene with an amino end is reacted with acryloyl chloride.

50 g of macromonomer Kerocom PIBA (0.05 mol), 6.06 g of triethylamine (0.06 mol) and 100 g of toluene are introduced into a 500 ml reactor with a central mechanical stirrer, a thermometer and a reflux condenser. The mixture is stirred in order to dissolve the reactants and is cooled in an ice bath. 5.43 g (0.06 mol) of acryloyl chloride in 20 g of toluene contained in a dropping funnel are placed above the reactor. This solution is added dropwise to the reactor with stirring while maintaining the temperature of the reaction mixture between 0° C. and 10° C. At the end of the addition, the temperature is allowed to rise to 25° C. and these conditions are maintained for 18 hours.

The toluene is evaporated from the reaction mixture and 300 g of dichloromethane are added. This solution is extracted with a 100 g/l aqueous NaCl solution, 300 g of saline solution being used. Extraction is carried out in a dropping funnel. Three successive extractions are thus carried out under the same conditions. Finally, the organic phase is recovered and dried with $Na_2SO_4$. The dichloromethane is subsequently distilled off on a rotary evaporator, in order to obtain the macromonomer with an acrylamido end.

The yield obtained is 72%.

The molecular mass at the GPC peak tip, measured by steric exclusion chromatography on microstyragel columns with tetrahydrofuran as eluent and polystyrene standards, is 2480.

EXAMPLE 8
Preparation of a Grafted Acrylic Copolymer from the Macromonomer (P) of Example 7

The grafted acrylic copolymer is prepared from the following composition:

| tert-Butyl acrylate | 70% by weight |
|---|---|
| Acrylic acid | 20% by weight |
| Macromonomer (P) of Example 7 | 20% by weight |

100 g of the mixture of monomers described above, 60 g of tetrahydrofuran and 40 g of cyclohexane, and 1 ml of 97% tert-butyl peroxy(2-ethylhexanoate) (sold by the company Akzo under the name Trigonox 21 S) are introduced into a 1 litre reactor with a central mechanical stirrer, a reflux condenser, a thermometer and nitrogen sparging. The mixture is stirred at room temperature under nitrogen sparging in order to be homogenized. The mixture is subsequently heated to 78° C. with stirring and nitrogen sparging. Reaction is allowed to take place under these conditions for 18 hours. At the end of the synthesis, the mixture is returned to room temperature and diluted with approximately 200 g of ethyl acetate, and the polymer is purified by precipitation of the solution from 6 l of petroleum ether. The precipitate is dried under vacuum at a temperature of 45° C. to constant weight.

The yield is 90%. The acid number is 167.

The characterization of the distribution of the molecular weights by steric exclusion chromatography gives 1 single main peak corresponding to a molecular weight of 54,300.

The glass transition temperature Tg of the skeleton, measured by DSC (differential scanning calorimetry), is 80° C.

EXAMPLE 9
Preparation of an Acrylic Copolymer Containing Poly(butyl acrylate) Grafts The grafted acrylic copolymer is prepared from the following composition:

| tert-Butyl acrylate | 60% by weight |
|---|---|
| Acrylic acid | 20% by weight |
| Poly (butyl) acrylate macromonomer with a Tg of −30° C. and with a number-average molecular weight of 6000, sold under the name AB-6 by Toa Gosei | 20% by weight |

100 g of the mixture of monomers described above, 100 g of ethanol and 1 ml of 97% tert-butyl peroxy(2-ethylhexanoate) (sold by the company Akzo under the name Trigonox 21 S) are introduced into a 1 litre reactor with a central mechanical stirrer, a reflux condenser, a thermometer and nitrogen sparging. The mixture is stirred at room temperature under nitrogen sparging in order to be homogenized. The mixture is subsequently heated to 78° C. with stirring and nitrogen sparging. Reaction is allowed to take place under these conditions for 18 hours. At the end of the synthesis, the mixture is returned to room temperature and diluted with approximately 200 g of ethyl acetate, and the polymer is purified by precipitation of the solution from 6 l of petroleum ether. The precipitate is dried under vacuum at a temperature of 45° C. to constant weight.

The yield is 85%. The acid number is 162.

The characterization of the distribution of the molecular weights by steric exclusion chromatography gives 1 single main peak corresponding to a molecular weight of 99,000.

The glass transition temperature Tg of the skeleton, measured by DSC (differential scanning calorimetry) is 80° C.

COMPOSITION EXAMPLES A, B AND C

EXAMPLE A
Aerosol Styling Spray

Composition A:

| | |
|---|---|
| Grafted acrylic copolymer of Example 5 | 8% by weight A.M. (A.M. active material) |
| 2-Amino-2-methyl-1-propanol for neutralization to 50% | q.s. for |
| Ethanol | q.s. for 100% by weight |

Pressurization:

| | |
|---|---|
| Composition A | 37% by weight |
| Dimethyl ether | 43% by weight |
| Pentane | 20% by weight |

EXAMPLE B
Aerosol Styling Spray

Composition B:

| | |
|---|---|
| Grafted acrylic copolymer of Example 6 | 5.4% by weight A.M. |
| 2-Amino-2-methyl-1-propanol for neutralization to 75% | q.s. for |
| Ethanol | q.s. for 100% by weight |

Pressurization:

| | |
|---|---|
| Composition B | 37% by weight |
| Dimethyl ether | 43% by weight |
| Pentane | 20% by weight |

EXAMPLE C
Pump-action Styling Spray

| | |
|---|---|
| Grafted acrylic copolymer of Example 5 | 2% by weight A.M. |
| 2-Amino-2-methyl-1-propanol for neutralization to 50% | q.s. for |
| Ethanol | q.s. for 100% by weight |

The three compositions A, B and C, after application to hair in styling finishing, contribute good setting to the hair with good ease of disentangling and a smooth and pleasant feel after brushing.

EXAMPLE D
Aerosol Styling Spray

Composition D:

| | |
|---|---|
| Grafted acrylic copolymer of Example 8 | 8% by weight A.M. |
| 2-Amino-2-methyl-1-propanol for neutralization to 50% | q.s. for |
| Ethanol | q.s. for 100% by weight |

Pressurization:

| | |
|---|---|
| Composition D | 50% by weight |
| Dimethyl ether | 50% by weight |

EXAMPLE E
Aerosol Styling Spray

Composition E:

| | |
|---|---|
| Grafted acrylic copolymer of Example 9 | 8% by weight A.M. |
| 2-Amino-2-methyl-1-propanol for neutraiization to 50% | q.s. for |
| Ethanol | q.s. for 100% by weight |

Pressurization:

| | |
|---|---|
| Composition E | 50% by weight |
| Dimethyl ether | 50% by weight |

The two compositions D and E, after application to the hair in styling finishing, contribute a good lacquering power to the hair without a sticky effect, good ease of disentangling and good removal with shampoos.

What is claimed is:

1. A cosmetic or dermatological composition comprising, in a cosmetically acceptable vehicle, at least one grafted copolymer, having a skeleton (S) which comprises a hydrophilic copolymer with a glass transition temperature Tg greater than 25° C., obtained by radical polymerization or by polycondensation, said skeleton further comprising at least one graft comprising a hydrophobic macromonomer (M) with a glass transition temperature T'g of less than 25° C.

2. A composition according to claim 1, wherein said macromonomer (M) comprises hydrocarbon, hydrofluorocarbon or fluorocarbon and has a phase transition temperature T'g of less than 25° C.

3. A composition according to claim 2, wherein said macromonomer (M) has a phase transition temperature T'g of less than 10° C.

4. A composition according to claim 3, wherein said macromonomer (M) has a phase transition temperature T'g of less than or equal to 0° C.

5. A composition according to claim 1, wherein said macromonomer (M) has a surface tension of less than or equal to 40 dyne/cm at 20° C.

6. A composition according to claim 1, wherein said macromonomer (M) has an average molecular weight, measured at the peak tip by steric exclusion chromatography, ranging from 200 to 20,000.

7. A composition according to claim 1, wherein said macromonomer (M) is:
   (a) a polymer or copolymer of linear or branched $C_2$–$C_{18}$ alkyl acrylate or methacrylate with a T'g of less than 25° C. and having a terminal group that is a vinyl, an allyl, a methallyl, a (meth)acryloyl, an ethacryloyl, a vinylbenzoyl, a vinylbenzyl, a $C_1$–$C_4$ alkenyl or a $C_1$–$C_6$ cycloalkenyl or a terminal reactive functional group capable of interacting with the skeleton (S) or the monomers constituting said skeleton or a terminal reactive functional group capable of participating in a polycondensation;
   (b) a polyolefin with a T'g of less than 25° C. and having a terminal group possessing ethylenic unsaturation or a terminal reactive functional group capable of interacting with the skeleton (S) or the monomers constituting the skeleton or a terminal reactive functional group capable of participating in a polycondensation;

(c) a vinyl polymer with a T'g of less than 25° C. and having a terminal group possessing ethylenic unsaturation or a terminal reactive functional group capable of interacting with the skeleton (S) or the monomers constituting the skeleton or a terminal reactive functional group capable of participating in a polycondensation;

(d) a polymer or copolymer of fluorinated or perfluorinated monomers with a T'g of less than 25° C. and having a terminal group having ethylenic unsaturation or a terminal reactive functional group capable of interacting with the skeleton (S) or the monomers constituting the skeleton or a terminal reactive functional group capable of participating in a polycondensation; or (e) a polyester with a T'g of less than 25° C. and having a terminal group possessing ethylenic unsaturation or a terminal reactive functional group capable of interacting with the skeleton (S) or the monomers constituting the skeleton or a terminal reactive functional group capable of participating in a polycondensation.

8. A composition according to claim 7, wherein said macromonomer is:

a poly(butyl acrylate) macromonomer with a monomethacrylate end;

a poly(2-ethylhexyl acrylate) macromonomer with a monoacrylate or monomethacrylate end;

a poly(dodecyl acrylate) or poly(dodecyl methacrylate) macromonomer;

a poly(stearyl acrylate) or poly(stearyl methacrylate) macromonomer;

a polyethylene macromonomer;

a polypropylene macromonomer;

a polyethylene/polypropylene copolymer macromonomer;

a polyethylene/polybutylene copolymer macromonomer;

a polybutadiene macromonomer;

a polyisoprene macromonomer;

a hydrogenated polybutadiene or hydrogenated polyisoprene macromonomer having 3 or 4 repeat units;

a perfluoroalkyl (meth)acrylate homopolymer or copolymer; or an aliphatic polyester comprising a long carbonaceous sequence.

9. A composition according to claim 8, wherein said macromonomer is a hydrogenated polybutadiene or hydrogenated polyisoprene macromonomer and is a phytol (3,7,11,15-tetramethylhexadec-2-en-1-ol) acrylate or methacrylate.

10. A composition according to claim 1, wherein said macromonomer (M) is present in the composition in an amount ranging from 1 to 60% by weight with respect to the total weight of said grafted copolymer.

11. A composition according to claim 1, wherein said at least one grafted copolymer has an average molecular weight, measured at the peak tip by steric exclusion chromatography, ranging from 10,000 to 5,000,000.

12. A composition according to claim 1, wherein said skeleton (S) has a phase transition temperature Tg of greater than or equal to 35° C.

13. A composition according to claim 1, wherein said skeleton (S) comprises a copolymer obtained by radical polymerization of:

(a) at least one monomer or a mixture of monomers (A) possessing ethylenic unsaturation, and (b) at least one monomer or a mixture of monomers (B) which are polar and hydrophilic and which possess ethylenic unsaturation.

14. A composition according to claim 1, wherein said skeleton (S) comprises a copolymer obtained by polycondensation of:

(a) at least one monomer or a mixture of monomers (A') which are polycondensable; and optionally (b) a monomer or a mixture of monomers (B'), which are polycondensable with the monomer or monomers (A'), having at least one hydrophilic functional group, said functional group contributing solubility or dispersability in water, alcoholic media or aqueous/alcoholic media, the monomers (A') and (B') being chosen so that the phase transition temperature Tg of the skeleton (S) is greater than 25° C.

15. A composition according to claim 14, wherein said skeleton (S) is a polycondensate selected from polyesters, polyamides, polyurethanes and polyester amides.

16. A composition according to claim 13, wherein said monomer (A) is:

an acrylic or methacrylic ester or amide obtained from a linear, a branched or a cyclic aliphatic alcohol or an aromatic alcohols;

a vinyl, allyl or methallyl ester or amide obtained from a linear, a branched or a cyclic aliphatic alcohol or an aromatic alcohol;

an olefin; or a fluorinated or perfluorinated acrylic or vinyl monomer, or a mixture thereof.

17. A composition according to claim 16, herein said monomer (A) is:

methyl (meth)acrylate, ethyl (meth)acrylate, propyl (meth)acrylate, butyl (meth )acryl ate, isobutyl (meth)acrylate, tert-butyl (meth)acryl ate, tert-butylacrylamide, vinyl acetate, vinyl propionate, vinyl benzoate, vinyl tert-butylbenzoate, ethylene, propylene, styrene or substituted styrene, or a mixture thereof.

18. A composition according to claim 13, herein said monomer (B) is an anionic, cationic, amphoteric, or non-ionic, hydrophilic polar monomer having ethylenic unsaturation, or a mixture thereof.

19. A composition according to claim 18, wherein said monomer (B) is anionic and is:

a monomer comprising at least one acidic functional group, in the free form, in the partially neutralized form or in the completely neutralized form;

a monomer comprising at least one sulphonic acid functional group, said functional in the free form, in the partially neutralized form or in the completely neutralized form; or a monomer comprising at least one phosphoric or phosphonic acid functional group, in the free form, in the partially neutralized form or in the completely neutralized form.

20. A composition according to claim 19, wherein said anionic monomer (B) is:

a monocarboxylic acid; a dicarboxylic acid or acid anhydride, or a monoester or a monoamide thereof;

vinyl- or styrenesulphonic acid; or 2-acrylamido-2-methylpropanesulphonic acid, said monomers being in the free form, in the partially neutralized form or in the completely neutralized form.

21. A composition according to claim 18, wherein said monomer (B) is cationic and comprises at least one amine functional group in the free form, in the partially neutralized form, in the completely neutralized form, in the partially quaternized form or in the completely quaternized form.

22. A composition according to claim 21, wherein said cationic monomer (B) is:

dimethylaminoethyl (meth)acrylate, dimethylaminoethyl-methacrylamide, vinylamine, vinylpyridine or diallyi-dimethylammonium chloride, said cationic monomer being in the free form, in the partially neutralized form, in the completely neutralized form, in the partially quaternized form or in the completely quaternized form.

23. A composition according to claim 18, wherein said monomer (B) is amphoteric and is a carboxybetaine or sulphobetaine obtained by partial or complete quaternization of monomers having ethylenic unsaturation and comprising an amine functional group by sodium salts of carboxylic acids having a mobile halide or by cyclic sultones.

24. A composition according to claim 18, wherein said monomer (B) is non-ionic:

an $C_1$–$C_4$ hydroxyalkyl (meth)acrylate;

an acrylamide;

N-vinylpyrrolidone; or ethylene glycol (meth)acrylate, diethylene glycol (meth)acrylate or a (meth)acrylate of polyethylene glycol having a hydroxyl or ether end.

25. A composition according to claim 1, wherein said at least one grafted copolymer is present in an amount ranging from 0.1 to 50% with respect to the total weight of the composition.

26. A composition according to claim 25, wherein said at least one grafted copolymer is present in an amount ranging from 1 to 30% with respect to the total weight of the composition.

27. A composition according to claim 1, wherein said cosmetically acceptable vehicle comprises water, at least one cosmetically acceptable organic solvent or a mixture of water and at least one cosmetically acceptable organic solvent.

28. A composition according to claim 27, wherein said cosmetically acceptable organic solvent is a lower $C_1$–$C_4$ alcohol.

29. A composition according to claim 1, wherein said grafted copolymer is; dissolved or dispersed in said vehicle.

30. A composition according to claim 1, further comprising at least one conventional cosmetic additive, wherein said additive is:

a mineral oil, a vegetable oil, an animal oil, a synthetic oil an animal wax, a fossil wax, a vegetable wax, a mineral wax, a synthetic wax, an organic solvent, a thickening agent, a softener, an anti-foaming agent, a moisturizing agent, a humectant, a treating agent, an antiperspirant, a basifying agent, an acidifying agent, a UV-A or UV-B or broad spectrum sunscreen, a dye, a pigment, a fragrance, a plasticizer, a preservative, an anionic organic polymer, a non-ionic organic polymer, an amphoteric organic polymer or a propellant.

31. A composition according to claim 1, wherein said composition is a hair composition, a make-up composition or a skin care composition.

32. A method for preparing a cosmetic or dermatological composition according to claim 1, said method including said at least one grafted copolymer in said comprising as a comprising film-forming agent or as an additive for said film-forming agent.

33. A process for the treatment of keratinous substances, comprising applying, to said keratinous substances, a composition as defined in claim 1.

34. A process according to claim 33, wherein said keratinous substances are hair, skin, or eyelashes.

* * * * *

UNITED STATES PATENT AND TRADEMARK OFFICE
CERTIFICATE OF CORRECTION

PATENT NO.    : 6,403,106 B1
DATED         : June 11, 2002
INVENTOR(S)   : Henri Sebag et al.

It is certified that error appears in the above-identified patent and that said Letters Patent is hereby corrected as shown below:

Column 14,
Line 30, "alcohols" should read -- alcohol --.
Line 37, "herein" should read -- wherein --.
Line 40, "butyl (meth )acryl ate" should read -- butyl (methe) acrylate --.
Line 41, "tert-butyl (meth)acryl ate" should read -- tert-butyl (meth)acrylate --.
Line 47, "herein" should read -- wherein --.
Line 57, after "said functional", insert -- group --.

Column 15,
Lines 12 and 13, "diallyidimethylammonium" should read
-- diallyldimethylammonium --.
Line 26, "an $C_1$-$C_4$" should read -- a $C_1$-$C_4$ --.

Column 16,
Line 10, after "is", delete the semicolon.
Line 15, after "synthetic oil", insert a comma.

Signed and Sealed this

Fifth Day of November, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO.   : 6,403,106 B1
DATED        : June 11, 2002
INVENTOR(S)  : Henri Sebag et al.

It is certified that error appears in the above-identified patent and that said Letters Patent is hereby corrected as shown below:

Column 14,
Line 30, "alcohols" should read -- alcohol --.
Line 37, "herein" should read -- wherein --.
Line 40, "butyl (meth )acryl ate" should read -- butyl (meth)acrylate --.
Line 41, "tert-butyl (meth)acryl ate" should read -- tert-butyl (meth)acrylate --.
Line 47, "herein" should read -- wherein --.
Line 57, after "said functional", insert -- group --.

Column 15,
Lines 12 and 13, "diallyidimethylammonium" should read
-- diallyldimethylammonium --.
Line 26, "an $C_1$-$C_4$" should read -- a $C_1$-$C_4$ --.

Column 16,
Line 10, after "is", delete the semicolon.
Line 15, after "synthetic oil", insert a comma.

Signed and Sealed this

Seventeenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.   : 6,403,106 B1
DATED        : June 11, 2002
INVENTOR(S)  : Henri Sebag et al.

It is certified that error appears in the above-identified patent and that said Letters Patent is hereby corrected as shown below:

Column 14,
Line 30, "alcohols" should read -- alcohol --.
Line 37, "herein" should read -- wherein --.
Line 40, "butyl (meth )acryl ate" should read -- butyl (meth)acrylate --.
Line 41, "tert-butyl (meth)acryl ate" should read -- tert-butyl (meth)acrylate --.
Line 47, "herein" should read -- wherein --.
Line 57, after "said functional", insert -- group --.

Column 15,
Lines 12 and 13, "diallyidimethylammonium" should read
-- diallyldimethylammonium --.
Line 26, "an $C_1$-$C_4$" should read -- a $C_1$-$C_4$ --.

Column 16,
Line 10, after "is", delete the semicolon.
Line 15, after "synthetic oil", insert a comma.

Signed and Sealed this

Fourteenth Day of January, 2003

JAMES E. ROGAN
*Director of the United States Patent and Trademark Office*